US005824650A

United States Patent [19]
De Lacharriere et al.

[11] Patent Number: 5,824,650
[45] Date of Patent: Oct. 20, 1998

[54] TOPICAL COMPOSITION CONTAINING A SUBSTANCE P ANTAGOINST

[75] Inventors: Olivier De Lacharriere, Paris; Lionel Breton, Versailles, both of France

[73] Assignee: L'Oreal, Paris, France

[21] Appl. No.: 575,682

[22] Filed: Dec. 19, 1995

[30] Foreign Application Priority Data

Dec. 19, 1994 [FR] France .................................. 94 15253

[51] Int. Cl.⁶ ......................... A61K 38/00; A61K 31/135
[52] U.S. Cl. ......................... 514/15; 514/210; 514/293; 514/305; 514/315; 514/410; 514/416; 514/422; 514/423; 514/426; 514/438; 514/461; 514/613; 514/617; 514/663; 514/646
[58] Field of Search ....................... 514/15, 646

[56] References Cited

U.S. PATENT DOCUMENTS

| | | |
|---|---|---|
| 3,772,431 | 11/1973 | Mlkvy et al. . |
| 3,888,976 | 6/1975 | Mlkvy et al. . |
| 4,477,439 | 10/1984 | D'Alelio . |
| 4,943,432 | 7/1990 | Biener . |
| 4,980,184 | 12/1990 | Gordon . |
| 4,986,981 | 1/1991 | Glace et al. . |
| 5,047,409 | 9/1991 | Di Schiena et al. . |
| 5,079,010 | 1/1992 | Natterer . |
| 5,091,171 | 2/1992 | Yu et al. . |
| 5,202,130 | 4/1993 | Grant et al. . |
| 5,569,662 | 10/1996 | Satake et al. ........................... 514/305 |

FOREIGN PATENT DOCUMENTS

| | | |
|---|---|---|
| 0217975 | 4/1987 | European Pat. Off. . |
| 0439640 | 8/1991 | European Pat. Off. . |
| 0459890 | 12/1991 | European Pat. Off. . |
| 0586929 | 3/1994 | European Pat. Off. . |
| 5394 | 10/1967 | France . |
| 2184890 | 6/1978 | France . |
| 3338957 | 5/1985 | Germany . |
| 0280692 | 7/1990 | Germany . |
| 0297062 | 1/1992 | Germany . |
| WO 96/19184 | 6/1996 | WIPO . |

OTHER PUBLICATIONS

Exp Eye Res, 50(1). 1990. 21–26, Beding–Barnekow et al, "Systemic and Intraocular . . . ", p. 25, col. 2, line 2.
Eur. J. Pharmacol., 1991, 209/3 (175–183), Netherlands, Andersson et al, "Ruthenium Red . . . ".
Br J. Dermatol, 124 (4). 1991. 324–328., Wallengren, "Substance P Antagonist . . . ".
Jancso–Gabor, "Action of rare earth metal complexes on neurogenic as well as on bradykinin–induced inflammation", J. Pharm. Pharmac.,22:366–371 (1970).
"La peau sensible, un authentique syndrome clinique", Le Quotidien du Medecin, No. 5747, Dec. 6, 1995; Cosmetologie, Therapeutique, No. 1511, Dec. 17, 1995.
Uy Dong Sohn et al, "Agonist–Independent, Muscle–Type–Specific Signal Transduction Pathways in Cat Esophageal and Lower Esophageal Sphincter Circular Smooth Muscle", J. of Pharmacology & Experimental Therapeutics,273:481–491 (1995).
Mitsuo Ishizawa, "Contractile Responses of Longitudinal Muscle Strip to 5–HT and Influences of Divalent Cations in the Guinea–Pig Isolated Colon", J. Smooth Muscle Res., 30:65–72 (1994).
H. Goodman, Cosmetic Dermatology, First Edition, Fourth Impression, p. 181 (1936).
Martindale, The Extra Pharmacopoeia, Twenty–seventh Edition, The Pharmaceutical Press, London, pp. 219, 1775 and 1814 (1977).
McGraw–Hill Dictionary of Scientific and Technical Terms, Fifth Edition, pp. 109 and 332 1995.
Sohn et al, Different Receptors Activate a Different Single G–Protein in Esophageal. (Gis) and in LES (Gq) Circular Smooth Muscle, Gastroenterology, vol. 104 (1993).
Maison G. deNavarre, The Chemistry and Manufacture of Cosmetics, 2nd Ed. vol. IV, p. 1261 (1975).
Alexander A. Fisher, "Irritant Reactions from Topical Urea Preparations Used for Dry Skin Advantages of a Urea–Free 'Dead Sea Salt' Cream", Current Contact News, vol. 18, pp. 761–772 (1976).
The United States Pharmacopeia, "Alumina/Drug Substances and Dosage Form", pp. 20 and 22 (1975).
Nordia Briefs, "A Salt–Containing Cream for Dry Skin", No. 484, Jan. 1978.
Cosmetic Counter, vol. 109, Oct. 1994.

Primary Examiner—Rebecca Cook
Attorney, Agent, or Firm—Burns, Doane, Swecker & Mathis, L.L.P.

[57] ABSTRACT

The invention relates to a therapeutic composition for topical application containing at least one product with an irritant side effect and a substance P antagonist for reducing or even eliminating the irritant effect of this product.

It also relates to the use of a substance P antagonist for the preparation of a pharmaceutical composition for topical application containing at least one product with an irritant side effect for reducing or even eliminating the irritant effect of this product.

The substance P antagonist may be a peptide compound or a nitrogen-containing compound or a nitrogen-, sulphur- or oxygen-containing heterocyclic compound.

16 Claims, No Drawings

TOPICAL COMPOSITION CONTAINING A SUBSTANCE P ANTAGOINST

The present invention relates to a topical therapeutic composition containing a substance P antagonist for reducing or even eliminating the irritant effects of certain pharmaceutical or dermatological active agents contained in such a composition.

In some skin diseases, such as acne, psoriasis, cutaneous lymphomas, verrucas, ulcers, precancerous lesions of the skin, and in the treatment of keratinization disorders and of skin disorders such as pustules, vibices, cicatrices, dyschromias, very dry skins, a number of active agents are used which have an irritant side effect.

For example, for the treatment of acne, retinoids, and especially retinoic acid, peroxides such as benzoyl peroxide, and hydroxy acids may be used.

Retinoids are also used for the treatment of keratinization disorders (Darier's disease, keratosis palmaris et plantaris, porokeratoses), vibices, photoageing, and psoriasis.

Peroxides are moreover also used for the treatment of leg ulcers (at a concentration of about 20%) and of chronic wounds.

Hydroxy acids are also used for the treatment of very dry skins, of ichthyosis, of cicatrices and of photoageing.

In the treatment of psoriasis, salicylic acid (in a proportion of 2 to 5% for example), anthranoids or anthralin, and vitamin D derivatives are used.

In a much higher proportion (30 to 50%), salicylic acid is used for the treatment of verrucas.

For the treatment of dyschromia, depigmenting agents such as hydroquinone are used.

Ascorbic acid is used to eliminate spots and cicatrices, especially cicatrices due to acne.

Antimetabolites such as caryolysine (chlormethine) are used to treat cutaneous T lymphomas (fungoid mycosis).

These active agents have the disadvantage of being irritant, and the more sensitive the skin, the more the subject treated feels this irritant effect.

Indeed, it is known that some skins are more sensitive than others. However, the symptoms of sensitive skins were up until now poorly characterized and the problem of these skins was, as a result, poorly defined; no one knew exactly the process involved in the sensitivity of the skin. Some thought that a sensitive skin was a skin which reacted to the products applied to the skin, others that it was a skin which reacted to certain external factors.

Because the characteristics of sensitive skins were poorly known, it was up until now very difficult to treat them, and they were indirectly treated, for example, by limiting, in the pharmaceutical or dermatological compositions, the use of products with an irritant character, such as the active agents indicated above, as well as other products involved in the composition, such as surfactants, preservatives and solvents.

The applicant has performed numerous clinical tests and has been able to determine the symptoms linked to sensitive skins. These symptoms are in particular subjective signs, which are essentially dysesthetic sensations. Dysesthetic sensations are understood to mean sensations which are painful to a greater or lesser degree in the cutaneous region such as pricking, formication, itching or pruritus, burns, inflammation, discomfort, stabbing pain and the like.

The applicant has now found that sensitive skins could be divided into two main clinical forms, irritable and/or reactive skins, and intolerant skins.

An irritable and/or reactive skin is a skin which reacts by a pruritus, that is to say by itching, or by pricking, to various factors such as the environment, emotions, foods, wind, rubbing, shaving, soap, surfactants, hard water with a high concentration of chalk, temperature variations or wool. In general, these signs are associated with a dry skin with or without dartres, or with a skin having an erythema.

An intolerant skin is a skin which reacts by sensations of inflammation, stabbing pain, formication and/or reddening, to various factors such as the environment, emotions, food and certain cosmetic preparations. In general, these signs are associated with a hyperseborrhoeic or acneic skin with or without dartres, and with an erythema.

In order to determine if a skin is sensitive or not, the applicant also developed a test. Indeed, after having carried out a large number of tests with the aim of defining a sensitive skin, it found surprisingly that there was a link between individuals with sensitive skin and those who reacted to a topical application of capsaicin.

The capsaicin test consisted in applying over about 4 $cm^2$ of skin 0.05 ml of a cream containing 0.075% of capsaicin and in noting the appearance of subjective signs caused by this application, such as pricking, burns and itching. In subjects with sensitive skins, these signs appear between 3 and 20 minutes after the application and are followed by the appearance of an erythema which starts at the periphery of the area of application.

Up until now, capsaicin was used as a medicinal product, in particular for treating zona pain. Capsaicin causes release of neuropeptides, and in particular of tachykinins which are derived from nerve endings of the epidermis and of the dermis. The applicant observed that the physiopathological pattern common to all conditions of sensitive skins was linked to a high capacity to release tachykinins and more particularly substance P in the skin. The dysesthetic manifestations which are caused by their release are described as "neurogenic".

This substance P is a polypeptide chemical element produced and released by a nerve ending. It is part of the family of tachykinins. Substance P is involved especially in the transmission of pain and in diseases of the central nervous system such as anxiety, schizophrenia, in respiratory and inflammatory diseases, in gastrointestinal diseases, in rheumatic diseases and in certain dermatological diseases such as eczema, psoriasis and contact dermatitis.

The applicant has now discovered that the essential characteristic of sensitive skins was linked to the release of substance P and that the use of substance P antagonists could make it possible to reduce or even eliminate the irritant effect of the irritant products.

According to the invention, irritant product is understood to mean the active agents intended for the treatment of cutaneous conditions, as well as the adjuvants contained in topical compositions, such as the solvents, surfactants and preservatives.

The applicant therefore envisaged the incorporation of a substance P antagonist into a therapeutic composition for topical application containing one or more products with an irritant side effect, in order to avoid or reduce the irritation caused by the presence of this or these product(s).

The substance P antagonist makes it possible especially to increase the quantity of active agent compared with the quantity normally used, for an enhanced efficacy.

Accordingly, the subject of the present invention is a therapeutic composition for topical application containing, in a pharmaceutically acceptable medium, at least one product with an irritant side effect, characterized in that it contains, in addition, at least one substance P antagonist.

The subject of the present invention is also the use of a substance P antagonist for the preparation of a therapeutic composition for topical application containing, in a pharmaceutically acceptable medium, at least one product with an irritant side effect, for reducing and/or eliminating this irritant effect.

Advantageously, this irritant product is a pharmaceutical or dermatological active agent.

In the composition of the invention, the aim of the substance P antagonist is to reduce and/or eliminate the irritant effect of these active agents, but it may, in addition, contribute to the treatment of the disease by virtue of its own therapeutic effect.

A pharmaceutically acceptable medium is a medium which is compatible with the skin, the nails, the mucous membranes and the hair. The composition containing the substance P antagonist may be applied to the face, the neck, the hair, the mucous membranes, the nails, the large skinfolds (inguinal, genital, axillary, popliteal, anal and submammary regions, and the elbow bends), or any other cutaneous region of the body.

In particular, the products with an irritant side effect are chosen from α-hydroxyacids (citric, malic, glycolic, tartaric, mandelic and lactic acids), β-hydroxyacids (salicylic acid and its derivatives), α-ketoacids, β-ketoacids, retinoids (retinol and its esters, retinal, retinoic acid and its derivatives, retinoids, especially those described in the documents FR-A-2,570,377, EP-A-199636, EP-A-325540, EP-A-402072), anthralins (dioxyanthranol), anthranoids, peroxides (especially benzoyl peroxide), minoxidil, lithium salts, antimetabolites, vitamin D and its derivatives, depigmenting agents (hydroquinone), surfactants (ionic or nonionic), preservatives, alcoholic solutions and solvents.

The use of a substance P antagonist makes it possible especially to multiply by 2 to 10 times the quantity of product, and more especially of active agent with an irritant side effect compared with the state of the art, without feeling all the abovementioned discomfort. Thus, hydroxyacids may be used up to 50% by weight of the composition and retinoids up to 5%, without any inconvenience.

For a substance to be recognized as a substance P antagonist, it should meet the following characteristic:
  it should have a pharmacological activity which antagonizes substance P, that is to say it should induce a coherent pharmacological response in at least one of the following two tests:
    the antagonistic substance should reduce extravasation of the plasma through the vascular wall induced by capsaicin or by an antidromic nervous stimulation, or alternatively
    the antagonistic substance should cause inhibition of the contraction of the smooth muscles induced by the administration of substance P.

The substance P antagonist may, in addition, have a selective affinity for the NK1 receptors for tachykinins.

The substance P antagonist of the invention may be functional or a receptor, that is to say may inhibit the synthesis and/or the release of substance P, or may prevent its binding and/or modulate its action.

Up until now, substance P antagonists were used to treat the diseases indicated above. To this end, reference may be made to the documents U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808, WO-A-93/01165, WO-A-93/10073 and WO-A-94/08997.

The substance P antagonist of the invention may be chosen especially from peptides and nonpeptide derivatives, and more specifically those containing a nitrogen-, sulphur- or oxygen-containing heterocycle, or the nitrogen-containing compounds containing a nitrogen atom linked directly or indirectly to a benzene ring.

Sendide and spantide II may be used in the invention, for example, as substance P-antagonizing peptide.

Sendide corresponds to the formula:

in which:
Tyr represents tyrosine,
D-Phe represents D-phenylalanine,
Phe represents phenylalanine,
D-His represents D-histidine,
Leu represents leucine,
Met represents methionine.
Spantide II corresponds to the formula:

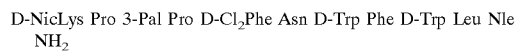

in which:
D-NicLys represents D-lysine nicotinate,
Pro represents proline,
3-Pal represents 3-pyridyl-alanine,
D-Cl₂Phe represents D-dichlorophenylalanine,
Asn represents asparagine,
D-Trp represents D-tryptophan,
Phe represents phenylalanine,
Leu represents leucine,
Nle represents norleucine.
The peptides described in the documents U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529 may also be used in the invention as substance P-antagonizing peptide.

Nonpeptide substance P antagonists which can be used in the invention are especially heterocyclic compounds, especially nitrogen-, sulphur- or oxygen-containing heterocyclic compounds, or compounds comprising a nitrogen atom linked directly or indirectly to a benzene ring.

As heterocyclic compound, there may be used in the invention those containing a nitrogen-containing heterocycle which are described in the following documents: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116 and WO-A-94/08997. In particular, the compound comprising at least one nitrogen-containing heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle, an isoindole derivative.

As other heterocyclic compounds, there may be mentioned the oxygen- or sulphur-containing heterocyclic compounds such as furan derivatives, benzofuran derivatives, thiophene derivative and benzothiophene derivatives, optionally containing nitrogen-containing substituents, such as the heterocyclic compounds described in the documents U.S. Pat. No. 4,931,459, U.S. Pat. No. 4,910,317 and EP-A-299457, and more especially the alkoxy and/or aryloxytetrazolyl-benzofuran-carboxamides or the alkoxy- and/or aryloxy-tetrazolylbenzothiophene-carboxamides.

As compounds containing a nitrogen atom linked directly or indirectly to a benzene ring, there may be mentioned those described in the following documents: EP-A-522808, WO-A-93/01165 and WO-A-93/10073. There may be mentioned especially the ethylenediamine derivatives, such as N,N'-bis-di(3,5-dimethylbenzyl)ethylenediamine and N,N'-bis-di(3,5-dimethoxybenzyl)ethylenediamine; these compounds are described as synthesis intermediates in the document WO-A-93/11338 filed in the name of the applicant.

The substance P antagonists may be synthesized or may be extracts of natural products (plant or animal products).

In the compositions according to the invention, the substance P antagonist is preferably used in a quantity ranging from 0.000001 to 5% by weight relative to the total weight of the composition, and in particular in a quantity ranging from 0.0001 to 0.1% by weight relative to the total weight of the composition.

The compositions according to the invention may be presented in all the galenic forms normally used for a topical application, especially in the form of aqueous, aqueous-alcoholic or oily solutions, of dispersions of the lotion or serum type, of anhydrous or lipophilic gels, of emulsions of liquid or semiliquid consistency of the milk type, which are obtained by dispersion of a fatty phase in an aqueous phase (O/W) or conversely (W/O), or of suspensions or emulsions of soft, semisolid or solid consistency, or alternatively of microemulsions, microcapsules, microparticles or of vesicular dispersions of the ionic and/or nonionic type. These compositions are prepared according to the customary methods.

The quantities of the various constituents of the compositions according to the invention are those conventionally used in the dermatological or pharmaceutical field.

These compositions constitute especially protective and treatment creams for the face, hands, feet, large anatomical skin-folds or for the body, protective or treatment body milks, antisun milks, lotions, gels or foams for the care or treatment of the skin and for protecting against sunlight, compositions against insect bites, compositions against pain, compositions for treating certain diseases of the skin such as those mentioned above.

The compositions may also be packaged in the form of an aerosol composition also containing a pressurized propelling agent.

The substance P antagonist may also be incorporated into various compositions for hair treatments, and especially shampoos, for example antiparasitic shampoos, treatment lotions, lotions or gels for preventing hair loss, and the like.

When the composition of the invention is an emulsion, the proportion of fatty phase may range from 5% to 80% by weight, and preferably from 5% to 50% by weight relative to the total weight of the composition. The oils, emulsifiers and coemulsifiers used in the composition in the form of an emulsion are chosen from those conventionally used in the dermatological field. The emulsifier and coemulsifier are present, in the composition, in a proportion ranging from 0.3% to 30% by weight, preferably from 0.5 to 20% by weight relative to the total weight of the composition. The emulsion may, in addition, contain lipid vesicles.

When the composition of the invention is an oily solution or gel, the fatty phase may represent more than 90% by weight of the total weight of the composition.

In a known manner, the composition of the invention may also contain the usual adjuvants in the dermatological field, such as hydrophilic or lipophilic gelling agents, hydrophilic or lipophilic additives, preservatives, antioxidants, solvents, perfumes, fillers, sunscreens, bactericides, odour absorbers and colouring matter. The quantities of these different adjuvants are those conventionally used in the pharmaceutical field, and are for example from 0.01% to 10% of the total weight of the composition. These adjuvants, depending on their nature, may be introduced into the fatty phase, into the aqueous phase and/or into the lipid spherules.

As oils which can be used in the invention, there may be mentioned mineral oils (liquid paraffin), vegetable oils (liquid fraction of shea butter, sunflower oil), animal oils (perhydrosqualene), synthetic oils (Purcellin oil), silicone oils (cyclomethicone) and fluorinated oils (perfluoropolyethers). Fatty alcohols, fatty acids (stearic acid) and waxes (paraffin, carnauba and beeswax) may be added to these oils.

As emulsifiers which can be used in the invention, there may be mentioned for example glycerol stearate, polysorbate 60 and the PEG-6/PEG-32/glycol stearate mixture sold under the name Tefose® 63 by the company Gattefosse and dimethicone copolyols, optionally in a mixture with cyclomethicones.

As solvents which can be used in the invention, the lower alcohols, especially ethanol and isopropanol may be mentioned.

As hydrophilic gelling agents, there may be mentioned the carboxyvinyl polymers (carbomer), the acrylic copolymers such as the copolymers of acrylates/alkyl acrylates, polyacrylamides, polysaccharides such as hydroxypropyl cellulose, clays and natural gums, and, as lipophilic gelling agents, there may be mentioned modified clays such as bentones, the metal salts of fatty acids such as aluminium stearates, hydrophobic silica, polyethylenes and ethyl cellulose.

The composition of the invention may also contain active agents other than the active agents having an irritant side effect.

As hydrophilic active agents, there may be used for example proteins or protein hydrolysates, amino acids, polyols, urea, allantoin, sugars and sugar derivatives, water-soluble vitamins, starch and plant extracts, especially those from Aloe vera.

As lipophilic active agents, tocopherol (vitamin E) and its derivatives, essential fatty acids, ceramides, essential oils and antiseptics may be used.

As other active agents, there may be mentioned by way of example:
   agents regulating cutaneous differentiation and/or proliferation and/or pigmentation such as oestrogens such as oestradiol or kojic acid;
   antibacterials such as clindamycin phosphate, erythromycin or antibiotics of the family of tetracyclines;
   antiparasitic agents, in particular metronidazole, crotamiton or pyrethrinoids;
   antifungal agents, in particular the compounds belonging to the family of imidazoles such as econazole, ketoconazole or miconazole or their salts, polyene compounds, such as amphotericin B, compounds of the family of allyl amines, such as terbinafine, or alternatively octopirox;

steroidal anti-inflammatory agents such as hydrocortisone, betamethasone valerate, clobetasol propionate, or non-steroidal anti-inflammatory agents such as ibuprofen and its salts, diclofenac and its salts, acetylsalicylic acid, acetaminophen or glycyrrhetinic acid;

anaesthetic agents such as lidocaine hydrochloride and its derivatives;

antipruritic agents such as thenaldine, trimeprazine or cyproheptadine;

antiviral agents such as acyclovir;

keratolytic agents such as the salts, amides or esters of alpha- and beta-hydroxycarboxylic or beta-ketocarboxylic acids;

anti-free radical agents such as alpha-tocopherol or its esters, superoxide dismutases, certain metal chelators;

antiseborrhoeic agents such as progesterone;

antidandruff agents such as octopirox or zinc pyrithione;

antiacne agents.

The following examples illustrate the invention. In these examples, the proportions indicated are percentages by weight.

EXAMPLE 1

Acne treatment cream for the face (oil-in-water emulsion)

| | |
|---|---|
| Sendide | 0.15% |
| Glycerol stearate | 2% |
| Polysorbate 60 (Tween 60 sold by the company ICI) | 1% |
| Stearic acid | 1.4% |
| n-octanoyl-5-salicylic acid | 1% |
| Triethanolamine | 0.7% |
| Carbomer | 0.4% |
| Liquid fraction of shea butter | 12% |
| Perhydrosqualene | 12% |
| Antioxidant | 0.05% |
| Perfume | 0.5% |
| Preservative | 0.3% |
| Water qs | 100% |

EXAMPLE 2

Emulsified care gel against insect bites (oil-in-water emulsion)

| | |
|---|---|
| Cyclomethicone | 3% |
| Purcellin oil (sold by the company Dragocco) | 7% |
| PEG-6/PEG-32/glycol stearate (Tefose ® 63 from Gattefosse) | 0.3% |
| Spantide II | 0.02% |
| Preservative | 0.3% |
| Perfume | 0.4% |
| Carbomer | 0.6% |
| Crotamiton | 5% |
| Glycyrrhetinic acid | 2% |
| Ethyl alcohol | 5% |
| Triethanolamine | 0.2% |
| Water qs | 100% |

EXAMPLE 3

Acne rosacea care cream for the face (oil-in-water emulsion)

| | |
|---|---|
| Spantide II | 0.25% |
| Glycerol stearate | 2% |
| Polysorbate 60 (Tween 60 sold by the company ICI) | 1% |
| Stearic acid | 1.4% |
| Metronidazole | 1% |
| Triethanolamine | 0.7% |
| Carbomer | 0.4% |
| Liquid fraction of shea butter | 12% |
| Liquid paraffin | 12% |
| Antioxidant | 0.05% |
| Perfume | 0.5% |
| Preservative | 0.3% |
| Water qs | 100% |

EXAMPLE 4

Gel for the treatment of acne

| | |
|---|---|
| All-trans-retinoic acid | 0.05% |
| N,N'-bis-di(3,5-dimethylbenzyl)-ethylenediamine | 5% |
| Hydroxypropyl cellulose (Klucel H sold by the company Hercules) | 1% |
| Antioxidant | 0.05% |
| Isopropanol | 40% |
| Preservative | 0.3% |
| Water qs | 100% |

EXAMPLE 5

Peeling lotion for the face

| | |
|---|---|
| Glycolic acid | 50% |
| Sodium hydroxide qs | pH 2.8 |
| Hydroxyethyl cellulose | 0.5% |
| N,N'-bis-di(3,5-dimethoxybenzyl)-ethylenediamine | 5% |
| Ethanol qs | 100% |

This lotion is used to remove the cicatrices left for example by acne.

EXAMPLE 6

W/O emulsion for the treatment of dry skins, or of xeroses

| | |
|---|---|
| Abil EM 90 from Goldschmidt (cetyldimethicone copolyol) | 2.5% |
| DC 344 fluid from Dow Corning (cyclomethicone) | 15% |
| DC 593 fluid from Dow Corning (cyclomethicone) | 3.5% |
| Witconol APM from Witco (polypropylene glycol-myristyl ether containing 3 mol of propylene glycol) | 6% |
| Sendide | 0.2% |
| Glycerine | 3% |
| Lactic acid | 5% |
| NH$_3$ (32% solution) qs | pH = 4 |
| NaCl | 0.6% |
| Preservative | 0.15% |
| Water qs | 100% |

EXAMPLE 7
Cream for the treatment of acne (dispersion of liposomes)

| | |
|---|---|
| Chimexane NS/dimyristyl phosphate (weight ratio 95/5) | 5% |
| Salicylic acid | 0.5% |
| N,N'-bis-di(3,5-dimethoxybenzyl)-ethylenediamine | 4% |
| Glycerine | 4% |
| Vegetable oil | 3% |
| Volatile silicone oil | 4.5% |
| Triclosan | 0.2% |
| Carboxyvinyl polymer | 0.9% |
| Sodium hydroxide | 1.8% |
| Preservatives | 0.8% |
| Water qs | 100% |

EXAMPLE 8
Cream for the treatment of acne (dispersion of liposomes)

| | |
|---|---|
| Chimexane NS | 5% |
| Glycolic acid | 0.8% |
| N,N'-bis-di(3,5-dimethylbenzyl)-ethylenediamine | 4% |
| Glyceryl | 4% |
| Hydrogenated isoparaffin | 3% |
| Carboxyvinyl polymer | 0.9% |
| Sodium hydroxide | 1.8% |
| Preservatives | 0.6% |
| Antioxidants | 0.2% |
| Water qs | 100% |

We claim:

1. A method of treating or preventing irritation to sensitive skin which occurs upon topical administration of at least one product which normally elicits an irritant side effect to sensitive skin if topically administered in the absence of an effective amount of a substance P antagonist, which comprises topically administering to a subject having sensitive skin a composition comprising (i) said product which normally elicits an irritant side effect, upon topical application to sensitive skin (ii) an amount of at least one substance P antagonist sufficient to reduce or eliminate said irritant side effect, and (iii) a pharmaceutically acceptable medium.

2. The method of claim 1, wherein the substance P antagonist is selected from the group consisting of a peptide, a compound comprising at least one heterocycle and a nitrogen-containing compound comprising at least one benzene ring.

3. The method of claim 1, wherein the amount of the substance P antagonist ranges from 0.000001 to 5% by weight relative to the total weight of the composition.

4. The method of claim 2, wherein the amount of the substance P antagonist ranges from 0.000001 to 5% by weight relative to the total weight of the composition.

5. The method of claim 3, wherein the amount of the substance P antagonist ranges from between 0.0001 to 0.1% by weight relative to the total weight of the composition.

6. The method of claim 4, wherein the amount of the substance P antagonist ranges from between 0.0001 to 0.1% by weight relative to the total weight of the composition.

7. The method of claim 1, wherein the substance P antagonist is a peptide.

8. The method of claim 7, wherein the peptide is sendide or spantide II.

9. The method of claim 1, wherein the product which causes an irritant side effect is selected from the group consisting of an α-hydroxyacid, a β-hydroxyacid, an α-ketoacid, a β-ketoacid, a retinoid, an anthralin, an anthranoid, a peroxide, minoxidil, a lithium salt, an antimetabolite, a vitamin D, a vitamin D derivative, a depigmenting agent, a surfactant and a solvent.

10. The method of claim 9, wherein the product which causes an irritant side effect is an α-hydroxyacid.

11. The method of claim 10, wherein the composition further comprises an active agent selected from the group consisting of a protein, a protein hydrolysate, an amino acid, a polyol, urea, a sugar, a sugar derivative, a vitamin, a starch, a plant extract, a ceramide, an essential oil and an antiseptic.

12. The method of claim 11, wherein the composition further comprises a polyol.

13. The method of claim 10, wherein the composition further comprises an agent selected from the group consisting of an antibacterial agent, an antiparasitic agent, an antifungal agent, an anti-inflammatory agent, an antipruritic agent, an anaesthetic, an antiviral agent, a keratolytic agent, an anti-free-radical agent, an antiseborrhoeic agent, an anti-dandruff agent, an antiacne agent and an agent which modulates at least one of cutaneous differentiation cutaneous proliferation, and cutaneous pigmentation.

14. The method of claim 13, wherein said additional agent is an antiacne agent.

15. The method of claim 1, wherein the substance P antagonist exhibits activity in at least one of the following assays:

(i) reduces extravasation of plasma through the vascular wall induced by capsaicin or by antidromic nervous stimulation; or (ii) inhibits the contraction of smooth muscles induced by substance P administration.

16. The method of claim 15, wherein the substance P antagonist further comprises selective affinity for the NK1 receptors for tachykinins.

* * * * *